US010869727B2

United States Patent
Yanof et al.

(10) Patent No.: US 10,869,727 B2
(45) Date of Patent: Dec. 22, 2020

(54) LIVE 3D HOLOGRAPHIC GUIDANCE AND NAVIGATION FOR PERFORMING INTERVENTIONAL PROCEDURES

(71) Applicant: THE CLEVELAND CLINIC FOUNDATION, Cleveland, OH (US)

(72) Inventors: Jeffrey H. Yanof, Solon, OH (US); Karl West, Geneva, OH (US); Sara Al-Nimer, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/405,875

(22) Filed: May 7, 2019

(65) Prior Publication Data

US 2019/0339525 A1 Nov. 7, 2019

Related U.S. Application Data

(60) Provisional application No. 62/667,687, filed on May 7, 2018.

(51) Int. Cl.
*A61B 34/20* (2016.01)
*G02B 27/01* (2006.01)
(Continued)

(52) U.S. Cl.
CPC .............. *A61B 34/20* (2016.02); *A61B 8/463* (2013.01); *A61B 8/466* (2013.01); *A61B 8/483* (2013.01);
(Continued)

(58) Field of Classification Search
CPC ............ G02B 27/0172; G02B 27/0093; G02B 27/017; G02B 2027/0138; A61B 8/463;
(Continued)

(56) References Cited

U.S. PATENT DOCUMENTS

| 6,019,724 A * | 2/2000 | Gronningsaeter ... A61B 8/0833 |
| | | 600/439 |
| 2005/0203380 A1* | 9/2005 | Sauer ..................... A61B 34/20 |
| | | 600/417 |

(Continued)

FOREIGN PATENT DOCUMENTS

WO 2016/162789 A2 10/2016

OTHER PUBLICATIONS

Kuzhagaliyev, Timur, et al. "Augmented reality needle ablation guidance tool for irreversible electroporation in the pancreas." Medical Imaging 2018: Image-Guided Procedures, Robotic Interventions, and Modeling. vol. 10576. International Society for Optics and Photonics, 2018, Mar. 13, 2018.

(Continued)

*Primary Examiner* — Darlene M Ritchie
(74) *Attorney, Agent, or Firm* — Tarolli, Sundheim, Covell & Tummino LLP

(57) ABSTRACT

An interventional procedure can be performed less invasively with live 3D holographic guidance and navigation. Advantageously, the 3D holographic guidance and navigation overcomes the limitations of conventional displays of medical images on standard 2D flat panel screens. The live 3D holographic guidance can utilize a 3D holographic visualization that is derived from complementary imaging modalities (e.g., ultrasound and computed tomography) to provide a complete holographic view of a portion of the patient's body to enable navigation of a tracked interventional instrument/device.

23 Claims, 7 Drawing Sheets

(51) Int. Cl.

| | |
|---|---|
| *A61B 8/00* | (2006.01) |
| *A61B 8/08* | (2006.01) |
| *G06K 9/32* | (2006.01) |
| *G06K 9/00* | (2006.01) |
| *G06F 3/01* | (2006.01) |
| *A61B 90/00* | (2016.01) |
| *A61B 34/10* | (2016.01) |
| *A61B 17/00* | (2006.01) |
| *G02B 27/00* | (2006.01) |
| *A61B 90/50* | (2016.01) |

(52) U.S. Cl.
CPC ........ *A61B 8/5238* (2013.01); *G02B 27/0172* (2013.01); *G06F 3/011* (2013.01); *G06K 9/00671* (2013.01); *G06K 9/3216* (2013.01); *A61B 8/4245* (2013.01); *A61B 2017/00216* (2013.01); *A61B 2034/107* (2016.02); *A61B 2034/2048* (2016.02); *A61B 2034/2051* (2016.02); *A61B 2034/2055* (2016.02); *A61B 2034/2063* (2016.02); *A61B 2090/365* (2016.02); *A61B 2090/368* (2016.02); *A61B 2090/378* (2016.02); *A61B 2090/502* (2016.02); *A61M 2205/507* (2013.01); *G02B 27/0093* (2013.01); *G02B 2027/0138* (2013.01); *G06F 3/012* (2013.01); *G06K 2009/3225* (2013.01); *G06K 2209/05* (2013.01)

(58) Field of Classification Search
CPC ....... A61B 8/466; A61B 8/483; A61B 8/5238; A61B 8/4245; A61B 8/465; A61B 8/462; A61B 34/20; A61B 2090/368; A61B 2090/365; A61B 2090/502; A61B 2090/372; A61B 2034/2048; A61B 2034/107; A61B 2034/2051; A61B 2034/2055; A61B 2090/378; A61B 2017/00216; G06K 9/3216; G06K 9/00671; G06K 2009/3225; G06K 2209/05; G06F 3/011; G06F 3/012; G06F 3/013; A61M 2205/507

See application file for complete search history.

(56) References Cited

U.S. PATENT DOCUMENTS

| | | | |
|---|---|---|---|
| 2013/0267838 A1 | 10/2013 | Fronk et al. | |
| 2014/0189508 A1 | 7/2014 | Granchi et al. | |
| 2014/0193053 A1 | 7/2014 | Kadoury et al. | |
| 2016/0143693 A1* | 5/2016 | Yilmaz | A61B 6/5235 600/424 |
| 2017/0258526 A1* | 9/2017 | Lang | A61B 17/1703 |
| 2017/0301088 A1* | 10/2017 | Bharat | A61B 5/4381 |
| 2017/0319172 A1* | 11/2017 | Harlev | A61B 8/08 |
| 2017/0367766 A1* | 12/2017 | Mahfouz | A61F 2/4603 |
| 2018/0140362 A1* | 5/2018 | Cal | A61B 34/20 |
| 2018/0168732 A1* | 6/2018 | Trousset | A61B 6/5211 |
| 2018/0200018 A1* | 7/2018 | Silva | A61B 34/20 |
| 2019/0107700 A1* | 4/2019 | Lee | A61B 90/20 |
| 2019/0350657 A1* | 11/2019 | Tolkowsky | A61B 46/20 |
| 2020/0107002 A1* | 4/2020 | Casas | H04N 13/156 |

OTHER PUBLICATIONS

PCT International Search Report and Written Opinion for corresponding International Application Serial No. PCT/US2019/031688, dated Oct. 17, 2019, pp. 1-16.

Liu, Fangyi, et al. "A three-dimensional visualisation preoperative treatment planning system in microwave ablation for liver cancer: a preliminary clinical application." International Journal of Hyperthermia 29.7 (2013): 671-677, Sep. 20, 2013.

Marescaux, Jacques, and Michele Diana. "Next step in minimally invasive surgery: hybrid image-guided surgery." Journal of pediatric surgery 50.1 (2015): 30-36, Oct. 22, 2014.

Phillips Ultrasound Fusion and Navigation, Koninklijke Philips N.V., Aug. 26, 2019 https://www.philips.iq/en/healthcare/product/HCNOCTN150/fusion-and-navigation-image-fusion-and-needle-navigation/documentation.

Ren, Hongliang, et al. "Treatment planning and image guidance for radiofrequency ablation of large tumors." IEEE journal of biomedical and health informatics 18.3 (2013): 920-928, Oct. 24, 2013.

* cited by examiner

LIVE 3D HOLOGRAPHIC GUIDANCE AND NAVIGATION FOR PERFORMING INTERVENTIONAL PROCEDURES

CROSS-REFERENCE TO RELATED APPLICATIONS

This application claims the benefit of U.S. Provisional Application No. 62/667,687, filed May 7, 2018, entitled "REAL-TIME (LIVE) 3D HOLOGRAPHIC GUIDANCE AND NAVIGATION FOR PERFORMING INTERVENTIONAL PROCEDURES". This provisional application is hereby incorporated by reference in its entirety for all purposes.

TECHNICAL FIELD

The present disclosure relates generally to interventional procedures and, more specifically, to systems and methods that provide live three-dimensional (3D) holographic guidance and navigation for performing interventional procedures.

BACKGROUND

Image guidance generally refers to the tracking of an interventional instrument/device used for a medical procedure through a patient's anatomy to a target location during an interventional procedure. The patient's anatomy is represented by preoperative and/or intraoperative images, and the tracked interventional instrument/device is registered to preoperative and/or postoperative images. For a broad range of diagnostic and therapeutic procedures, ultrasonography can be used to track the interventional instrument/device. However, using ultrasonography to track the interventional instrument/device complicates the image guidance. First, ultrasonography can only be used to track the interventional instrument/device inside the patient's body and cannot track the interventional instrument/device before it enters the patient's body. Once inside the patient's body, a relationship between an ultrasound probe, the interventional device/instrument, the target location, and the imaging plane of the ultrasound probe can be unclear, complicating the alignment of the interventional instrument/device to the target location. Additionally, traditionally, images of the target location and the interventional instrument/device are displayed on a flat, 2D monitor at tableside, further complicating the maneuverability of the interventional instrument. For example, the 2D display makes the medical professional translate a position of the instrument/device and trajectory of the instrument/device relative to the target location into physical trajectory adjustments that are needed to correct the path of the instrument; this mental translation from 2D to 3D is quite difficult during the medical procedure.

SUMMARY

The present disclosure relates to systems and methods that provide live three-dimensional (3D) holographic guidance and navigation for performing interventional procedures.

In one aspect, the present disclosure can include a method for providing live 3D holographic guidance for performing an interventional procedure. The method can be performed by a head-mounted device that includes a processor and a head tracking mechanism, which can receive live tracking data in 3D-Cartesian coordinates of a navigation system. The live tracking data can include position and orientation of a tracked physical ultrasound transducer/probe connected to an ultrasound system, a tracked physical interventional device/instrument, and physical fiducial location sensors at specific anatomical locations on a physical patient. The physical head-mounted device can receive a live image stream acquired by the physical ultrasound transducer/probe connected to the ultrasound system; transform the live tracking data to the headset coordinate system; and display a live holographic projection of the live image stream in the headset coordinate system. The ultrasound image stream extends from the tracked physical ultrasound probe/transducer with the tracked position and tracked orientation of the probe/transducer. The live holographic projection is scaled to the physical anatomy consistent with an operator's view assessed with the head-tracking mechanism. The physical head-mounted device can then retrieve digital anatomical objects derived from pre-operative 3D computed tomography (CT) image data of the physical patient; transform the digital anatomical objects from the 3D CT coordinate system to the headset coordinate system; translate the anatomical objects in the headset coordinate system by a 3D vector computed based on a 3D point location on the live holographic projection of the live image stream and a corresponding point within the stored pre-operative CT image data in the headset coordinate system to correct for an anatomical change of the physical patient; and display a holographic visualization comprising a holographic representation of the tracked physical interventional device/instrument congruent with the registered holographic projection of the live ultrasound image stream and the holographic anatomical objects derived from CT. The three holographic projections, from viewpoints determined by the head-tracking mechanism, are used to navigate the tracked physical ultrasound probe and guide the physical interventional device/instrument to the therapeutic target.

In another aspect, the present disclosure can include a system that provides live 3D holographic guidance for performing an interventional procedure. The system includes a computing device comprising a memory to store digital anatomical objects derived from pre-operative 3D computed tomography (CT) image data of a physical patient. The CT image data is in 3D coordinates of a CT coordinate system. The system also includes a head-mounted device, comprising a processor and a head-tracking mechanism, to: receive live tracking data in 3D Cartesian coordinates of a navigation system, wherein the live tracking data comprises a position and orientation of: a tracked physical ultrasound transducer/probe connected to an ultrasound system, a tracked physical interventional device/instrument, and physical fiducial location sensors at specific anatomical locations on a physical patient; receive a live image stream acquired by the physical ultrasound transducer/probe connected to the ultrasound system; transform the live tracking data to the headset coordinate system; display a live holographic projection of the live image stream in the headset coordinate system, wherein the ultrasound image stream extends from the tracked physical ultrasound probe/transducer with the tracked position and tracked orientation of the probe/transducer, wherein the live holographic projection is scaled consistent with an operator's view assessed with the head-tracking mechanism; retrieve the digital anatomical objects; transform the digital anatomical objects from the 3D coordinates of the CT coordinate system to the headset coordinate system; translate the anatomical objects in the headset coordinate system by a 3D vector computed based on a 3D point location on the live holographic projection of the live image stream and a corresponding point within the stored pre-operative CT image data in the headset coordinate system to correct for an anatomical change of the physical patient; and display a holographic visualization comprising a holographic representation of the tracked physical interventional device/instrument congruent with the registered holographic projection of the live ultrasound image stream and the holographic anatomical objects derived from CT, wherein the three holographic projections, from viewpoints determined by the head-tracking mechanism, are used to position the tracked physical ultrasound probe and guide the physical interventional device/instrument to the therapeutic target.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
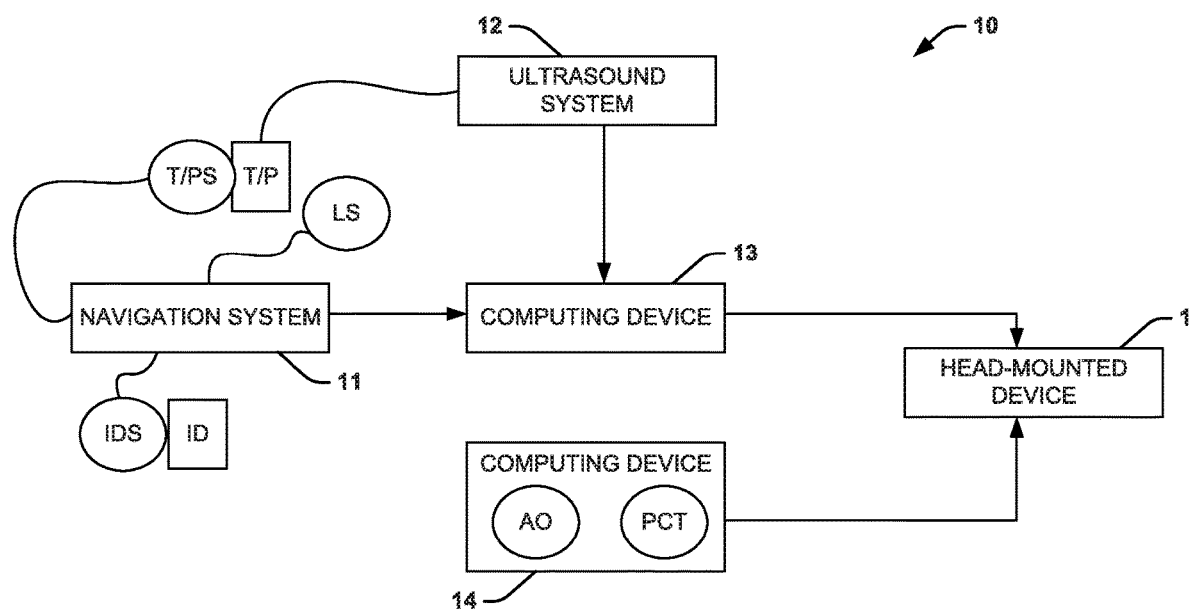
FIG. 1 is a block diagram showing an example of a system that provides live three-dimensional (3D) holographic guidance and navigation for performing interventional procedures in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "interventional procedure" refers to a medical procedure used for diagnosis or treatment that involves accessing the inside of a patient's body. An interventional procedure can be a percutaneous non-vascular procedure (e.g., nerve block, biopsy, tumor ablation, etc.), a percutaneous vascular procedure (e.g., stent graft placement, virtual histology, fractional flow reserve, etc.), or an open surgical procedure (e.g., mitral valve replacement, tricuspid valve replacement, a minimally invasive procedure, etc.).

As used herein, the terms "interventional instrument/device" and "interventional device/instrument" refer to any tool used within the patient's body to facilitate an interventional procedure.

As used herein, the term "tracking data" refers to information measured in a tracking coordinate system by a navigation system related to an observation of one or more objects and may or may not be undergoing motion. The objects can include a tracked physical ultrasound transducer/probe connected to an ultrasound system, a tracked physical interventional device/instrument, physical fiducial location sensors, etc.

As used herein, the term "tracking coordinate system" refers to a 3D Cartesian coordinate system that uses one or more numbers to determine the position of points or other geometric elements unique to the particular tracking system. For example, the tracking coordinate system can be rotated, scaled, or the like, from a standard 3D Cartesian coordinate system.

As used herein, the term "head-mounted device" or "headset" refers to a display device, configured to be worn on the head, that has one or more display optics (including lenses) in front of one or more eyes. An example of a head-mounted device is a Microsoft HoloLens.

As used herein, the term "headset coordinate system" or "world coordinate system" refers to a 3D Cartesian coordinate system that uses one or more numbers to determine the position of points or other geometric elements unique to the particular head-mounted device system. For example, the headset coordinate system can be rotated, scaled, or the like, from a standard 3D Cartesian coordinate system.

As used herein, the term "imaging stream" refers to a real-time ultrasonography image of a portion of a patient's body.

As used herein, the term "anatomical objects" refers to discrete portions of a pre-operative CT image of a portion of a patient's body. The anatomical objects, in some instances, have been taken from the original pre-operative CT image.

As used herein, the term "CT coordinate system" refers to a 3D Cartesian coordinate system that uses one or more numbers to determine the position of points or other geometric elements unique to the particular CT imaging system. For example, the imaging coordinate system can be rotated, scaled, or the like, from a standard 3D Cartesian coordinate system.

As used herein, the term "hologram", "holographic projection", or "holographic representation" refers to a computer-generated image projected to a lens of a headset. Generally, a hologram can be generated synthetically (in an augmented reality (AR)) and is not related to physical reality.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time dimension) would be encompassed by the definition of three-dimensional or 3D.

As used herein, the terms "real-time" and "live" refer to the actual time during which a process or event occurs. In other words, a real-time event is done live (within milliseconds so that results are available immediately as feedback). For example, a real-time event can be represented within 100 milliseconds of the event occurring.

As used herein, the term "depth" can refer to an indication of how deep within a patient's body an image is (e.g., in centimeters). The depth can relate to scale.

As used herein, the terms "subject" and "patient" can be used interchangeably and refer to any vertebrate organism.

II. Overview

The present disclosure relates generally to interventional procedures, where an interventional instrument/device is guided or navigated through a patient's body. Traditionally, using ultrasonography (also referred to as "ultrasound", "sonography", "echo", and similar terms herein) to track the interventional instrument/device complicates the image guidance at least because ultrasonography can only be used to track the interventional instrument/device inside the patient's body and cannot track the interventional instrument/device before it enters the patient's body; once inside the patient's body, a relationship between an ultrasound probe, the interventional device/instrument, the target location, and the imaging plane of the ultrasound probe can be unclear, complicating the alignment of the interventional instrument/device to the target location; and, traditionally, images of the target location and the interventional instrument/device are displayed on a flat, 2D monitor at tableside, further complicating the maneuverability of the interventional instrument (e.g., requiring the medical professional to translate a position of the instrument/device and trajectory of the instrument/device relative to the target location into physical trajectory adjustments that are needed to correct the path of the instrument). The present disclosure reduces the traditional complexities caused by using ultrasonography to track the interventional instrument/device through a patient's body. Indeed, the present disclosure describes systems and methods that provide live three-dimensional (3D) holographic guidance and navigation for performing ultrasound-guided interventional procedures.

A 3D holographic visualization can include a holographic representation of the tracked interventional instrument/device displayed in congruence with a holographic projection of a live ultrasound image stream and holographic anatomical objects derived from a pre-operative image (all of the data being transformed into a common holographic coordinate system). Notably, the anatomical objects can be translated to accommodate for an anatomical change of the patient (e.g., breathing) by a 3D vector computed based on a 3D point location on the live holographic projection of the live ultrasound image stream (also referred to as "live image stream") and a corresponding point within the stored pre-operative CT image data in the headset coordinate system.

III. Systems

One aspect of the present disclosure can include a system 10 (FIG. 1) that provides live three-dimensional (3D) holographic guidance and navigation for an interventional procedure performed on a patient (also referred to as a "physical" patient). The interventional procedure can be any procedure that uses an imaging modality (e.g., ultrasonography, computed tomography, etc.) to provide guidance. In particular, the 3D holographic guidance and navigation of an interventional instrument can involve a fusion of two imaging modality—a fusion of a live ultrasound image and a pre-operative computed tomography imaged. For example, ultrasonography can be used to guide any interventional procedure used for diagnosis or treatment that involves accessing the inside of a patient's body, including percutaneous non-vascular procedures (e.g., nerve block, biopsy, tumor ablation, etc.), percutaneous vascular procedures (e.g., stent graft placement, virtual histology, fractional flow reserve, etc.), and open surgical procedures (e.g., mitral valve replacement, tricuspid valve replacement, a minimally invasive procedure, etc.). The live 3D holographic guidance and navigation can be provided for any procedure where ultrasonography is used to guide an interventional device.

The system 10 can use an augmented reality 3D holographic display to provide the live 3D holographic guidance and navigation, which can replace or otherwise enhance traditional 2D guidance. The system 10 can include a head-mounted device 1 that can be configured to generate the augmented reality 3D holographic display based on patient-specific and interventional procedure-specific data received from computing devices 13 and 14. It should be noted that computing devices 13 and 14 can be separate devices (both local to the head-mounted device 1, one local to and the other remote from the head-mounted device 1, both remote from the head-mounted device 1, etc.), but may be part of the same device. As an example, the head-mounted device can be an optical see through device.

The computing device 13 can receive data from an ultrasound system 12 (live image stream data) and a navigation system 11 (tracking data). The computing device 13 can be coupled to the ultrasound system 12 and the navigation system 11 according to wired connections and/or wireless connections. The computing device 13 can also be coupled to the head-mounted device 1 according to a wired connection and/or a wireless connection. It should be understood that the connections between the computing device 13 and the navigation system 11, the ultrasound system 12, and the head-mounted device can be independent from one another.

The ultrasound system 12 can send an ultrasound signal to the ultrasound transducer/probe (also referred to as a "physical" ultrasound transducer/probe) and receive a live image stream from the ultrasound transducer/probe T/P during the interventional procedure and provide the live image stream to the computing device 13. For example, the ultrasound transducer/probe T/P can be a B-mode probe, a linear probe, an intravascular ultrasound probe, or any other type of ultrasound transducer or probe. The live image stream can be in 2D. The computing device 13 can be coupled to the ultrasound system 12 according to a wired connection and/or a wireless connection configured for real time data transmission of the live image stream. For example, the live data stream can be transmitted between the ultrasound system 12 and the computing device 13 according to an HDMI connection.

The navigation system 11 can receive signals including live tracking data associated with tracking devices T/PS, IDS, and LS (also referred to as "physical" tracking devices) and send the live tracking data to the computing device 13. One or more tracking devices T/PS can be on and/or within the ultrasound transducer/probe T/P. One or more tracking devices IDS can be on and/or within an interventional device ID used during the interventional procedure. One or more tracking devices LS can be located at constant points on and/or near the patient's body. For example, the one or more tracking devices LS can be at fiducial locations on the patient's body. As another example, the one or more tracking devices LS can be at locations external to the patient's body. As a further examples, the one or more tracking devices LS can be at fiducial locations on the patient's body and at locations external to the patient's body. The tracking data can include position information and orientation information (each in three dimensions) from each of a plurality of tracking devices T/PS, IDS, and LS. The navigation system 11 can include components utilized to generate a signal used for tracking (e.g., based on a signal from the components, the tracking data can be generated). For example, the components can include an electromagnetic (EM) field generator, which can generate an electromagnetic field and the tracking devices T/PS, IDS, and LS, which can be sensors (e.g., coil-type sensors), respond by producing the tracking data. As another example, the components can include an optical generator and the tracking devices T/PS, IDS, and LS, which can be reflective markers, can be optically tracked to provide the tracking data. The computing device 13 can be coupled to the navigation system 11 according to a wired connection and/or a wireless connection configured for real time data transmission of the tracking data. For example, the tracking data can be transmitted between the navigation system 11 and the computing device 13 according to a serial connection. It should be noted that the navigation system 11 described herein can utilize tracking using fiducial markers. It will be understood that other navigation and tracking mechanisms can be used without departing from the spirit of this disclosure.

The computing device 14 can provide preoperative data (e.g., anatomical objects AO derived, e.g., by image segmentation, from preoperative computed tomography PCT images and/or the pre-operative computed tomography images PCT) related to the patient's anatomy to the head-mounted device 1. For example, the anatomical objects AO can be CT-based holograms of a portion of the patient's body. The computing device 14 can be connected to the head-mounted device according to a wired connection and/or a wireless connection. In some instances, the computing device 14 (or another computing device) can provide information related to a treatment plan related to the interventional procedure to the head-mounted device 1. In response to the treatment plan, the head-mounted device 1 can provide a projection to an operative site, dynamic registration, planned and tracked HLRs, and holographic zones for the occurrence of the interventional procedure.

Figure 2:
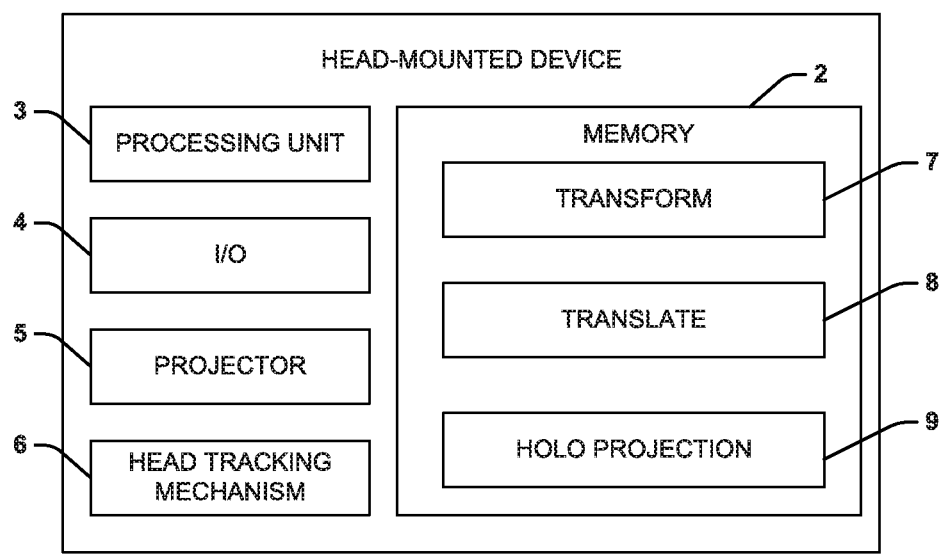
FIG. 2 is a block diagram showing an example of the head-mounted device of FIG. 1.

A representation of the head-mounted device 1 is shown in FIG. 2. The head-mounted device 1 can include a non-transitory memory 2 and a processing unit 3 (that may include one or more hardware processors) that can access the non-transitory memory 2 and execute instructions stored thereon to aid in the generation and display of the holographic display. For example, the non-transitory memory 2 can store instructions, such as transform 7, corrective translate 8 (or adjustment), and holo projection 9, which can be executed by the processing unit 3. The head-mounted device 1 can also include an input/output (I/O) 4 to communicate bi-directionally with computing devices 13 and 14. Additionally, the head-mounted device 1 can include a projector, which can facilitate the display the 3D hologram. Further, the head-mounted device 1 can also include a head tracking mechanism 6 that can aid in the performance of various actions based on a motion of the head of someone wearing the head-mounted device 1. The head-mounted device 1 can also include additional components—such as, a camera and/or other visualization and/or recording elements.

An example of the operation of the head-mounted device 1 is described below. Through the I/O 4 (which can be a wireless transmitter and/or receiver), the head-mounted device 1 can receive the live tracking data and the live image stream from computing device 13 and the preoperative data (e.g., anatomical objects AO derived from preoperative computed tomography PCT images and/or the pre-operative computed tomography images PCT and/or the treatment plan) from computing device 14. The live tracking data is in coordinates of a tracking coordinate system. At least a portion of the preoperative data is generally in coordinates of a CT coordinate system.

The transform 7 instruction stored in the non-transitory memory 2 and executed by the processing unit 3 can transform all of the received data into a common coordinate system (the headset coordinate system). For example, the live tracking data can be transformed from coordinates of a tracking coordinate system to the common coordinates of the headset coordinate system; the preoperative data can be transformed from coordinates of a CT coordinate system to the common coordinates of the headset coordinate system.

The holo projection 9 instruction stored in the non-transitory memory 2 and executed by the processing unit 3 can be used to generate the augmented reality 3D holographic display. The augmented reality 3D holographic display can include a live holographic projection of the live image stream in the headset coordinate system. The live image stream can be ore-calibrated with local rotation, translation, and scaling and automatically recalibrated so to maintain congruence with the patient's physical anatomy. For example, the live holographic projection of the live image stream can extend from the tracked physical ultrasound probe/transducer with the tracked position and tracked orientation of the probe/transducer, and the live holographic projection can be scaled to the physical anatomy consistent with an operator's view assessed with the head-tracking mechanism. The augmented reality 3D holographic display can also include a holographic projection of the anatomical objects registered to the live holographic projection. The anatomical objects can be projected to enable visualization without occlusion of the holographic ultrasound plane. The augmented reality 3D holographic display can include a holographic representation of the tracked physical interventional device/instrument congruent with the registered holographic projection of the live ultrasound image stream, which can also be congruent with a registered holographic projection of the anatomical objects.

The holographic representation of the tracked physical interventional device can be displayed with reference graphics related to an operative site corresponding to at least a portion of the patient's anatomy (which can be based on the treatment plan) and other guidance control graphics. The reference graphics and the guidance control graphics can provide guidance (e.g., visual guidance (pictorial, type, annotation, etc.) and/or auditory guidance) for tracking the physical interventional device through the patient's anatomy using the holographic guidance (using the 3D anatomical holographic projections and the 3D holographic representation of the interventional device). For example, when a line (or graphic) associated with the reference graphics and a line (or graphic) associated with the guidance control graphics intersect, the physical interventional device can be in alignment with a trajectory that would facilitate placement of the physical interventional device within the vasculature. This can be accompanied by a holographic annotation that reports the distance and/or angle deviation from a targeted position or orientation. The reference graphics and the guidance control graphics can be used to provide event driven guidance. For example, when a stent is within the patient's vasculature, the reference graphics and the guidance control graphics can provide auditory and/or visual guidance as the stent moves. As the stent is moved through the patient's vascular tree, a beep can be used to indicate proximity to a target location for the stent. Similarly, graphics can provide real-time annotations of the position and the orientation of the stent and/or showing the intersection with the target position. In other words, the event driven guidance can inform a user when they are on the right track using one or more event driven signals.

The projector 5 subsystem can display the augmented reality 3D holographic display. For example, the 3D holographic display can be stereoscopically projected onto the patient in congruence with the patient's physical anatomy as a visualization. The visualization can be scaled and/or moved according to an input from the head tracking mechanism 6 and/or an auditory input. Additionally, viewpoints can be determined based on inputs from the head tracking mechanism 6 (which can track the head within the head-mounted display 1 according to accelerometer(s), gyroscope(s), and/or magnetometer(s)). Upon receiving an operator input, projecting, by the head mounted device, the visualization can be displayed not congruent with the patient's physical anatomy and/or the physical ultrasound transducer/probe and/or the physical interventional device while maintaining co-registration of the holographic projections. Upon receiving another operator input, the visualization can be continuously realigned to re-orient the virtual display so that it always faces the operator based on tracking data from the head tracking mechanism 6. Upon receiving another operator input, the visualization can be translated, rotated, and/or scaled relative to the physical anatomy, and the elements can be co-registered. The rotation of the holographic scene can be limited or prevented to maintain hand-eye coordination of the operator when navigating the ultrasound transducer/probe (T/P) and the interventional device (ID). Based on the inputs, the tracked physical ultrasound probe (T/P) can be used to track and guide the physical interventional device/instrument (ID) to a therapeutic target (determined according to the pre-operative planning information).

The corrective translate 8 instruction stored in the non-transitory memory 2 and executed by the processing unit 3 can be used on the preoperative data to correct for an anatomical change of the physical patient (e.g., respiratory motion, gross patient motion, etc.). The corrective translation 8 instruction aids in the performance of a 3D translation and adjustment for improved registration between CT and ultrasound. As an example, the translate 8 instruction can be used to increase the registration between a preoperative CT image and a live ultrasound image. The pre-operative anatomical objects (AO) in the headset coordinate system can be translated by a 3D vector that is computed based on a 3D point location on a live holographic projection of the live image stream in the headset coordinate system and a corresponding point within the pre-operative CT image data in the headset coordinate system. The point location can be identified and located on the holographic projection of the live ultrasound image based on an operator input. For example, the point can be a center of an imaged tumor or blood vessel cross section.

IV. Methods

Another aspect of the present disclosure can include a method for providing live 3D holographic guidance and navigation for performing ultrasound-guided interventional procedures. The method is split between FIGS. 3 and 4 as partial methods 30 and 40. The methods 30 and 40 can be executed by hardware—for example, by the head-mounted device 1, shown in FIGS. 1 and 2, described above.

The methods 30 and 40 are illustrated as process flow diagrams with flowchart illustrations. For purposes of simplicity, the methods 30 and 40 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40. Additionally, one or more elements that implement the methods 30 and 40, such as head-mounted device 1 of FIGS. 1 and 2, may include a head-tracking mechanism, a non-transitory memory, and one or more processors that can facilitate the holographic image-guidance.

Figure 3:
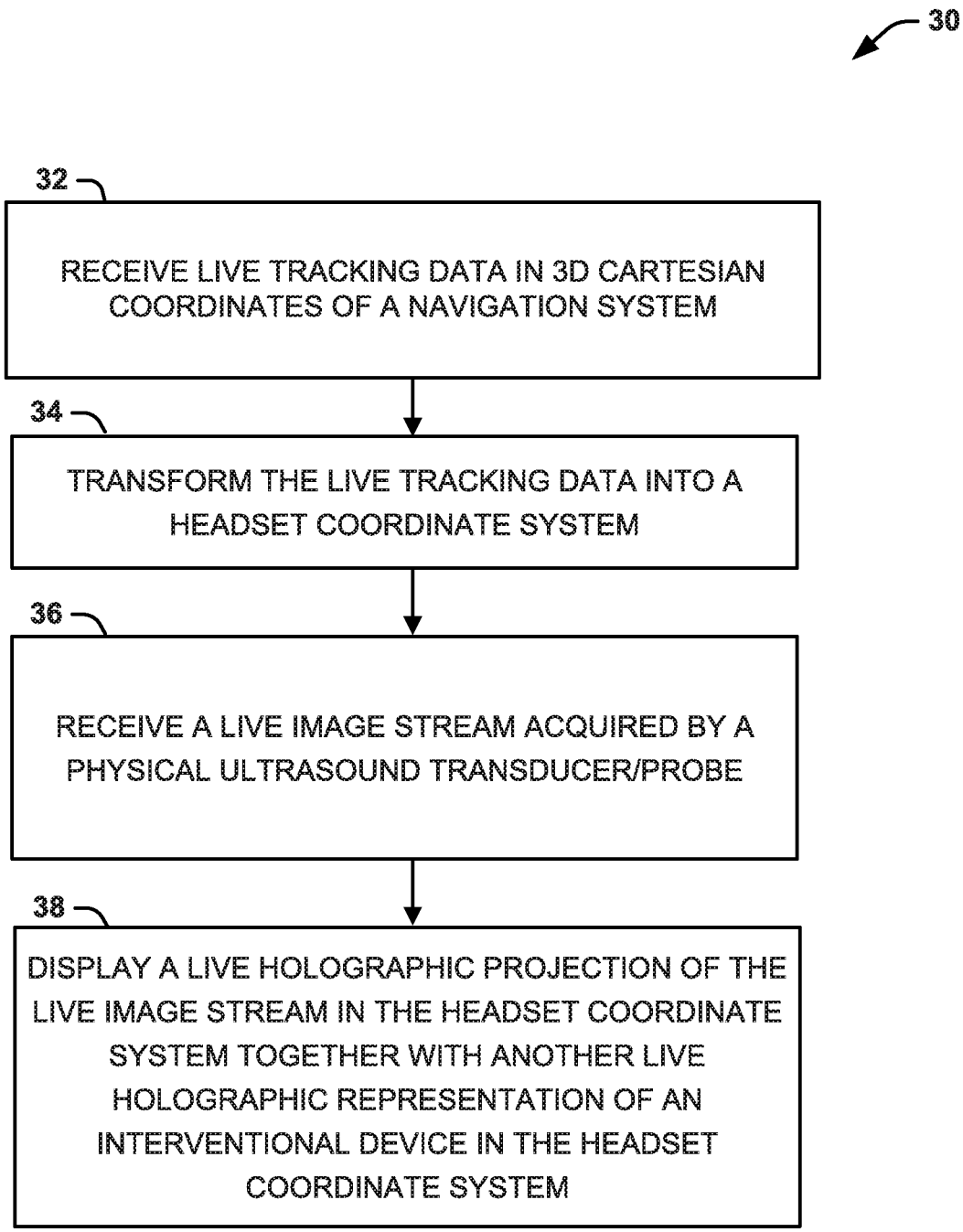
FIGS. 3 and 4 are process flow diagrams of example methods for providing live 3D holographic guidance and navigation for performing interventional procedures in accordance with another aspect of the present disclosure.

Referring now to FIG. 3, illustrated is a method 30, which is a portion of a larger method for providing live 3D holographic guidance and navigation for performing ultrasound-guided interventional procedures. At step 32, live data can be received (by head-mounted device 1) in 3D Cartesian coordinates of a navigation system (e.g., live tracking data from sensors on the ultrasound transducer probe T/PS, sensors on/within the interventional device IDS, and sensors at fiducial locations LS provided to the head-mounted device 1 by navigation system 11). It should be noted that the navigation system 11 described herein can utilize tracking using fiducial markers. It will be understood that other navigation and tracking mechanisms can be used without departing from the spirit of this disclosure. At step 34, the live tracking data can be transformed into a headset coordinate system (by head-mounted device 1). At step 36, a live image stream (acquired by an ultrasound transducer/probe T/P) can be received (by head-mounted device 1). At step 38, a live holographic projection of the live image stream in the headset coordinate system (determined with at least a portion of the live tracking data) can be displayed (by the head-mounted device 1) together with another live holographic representation of an interventional device in the headset coordinate system.

Figure 4:
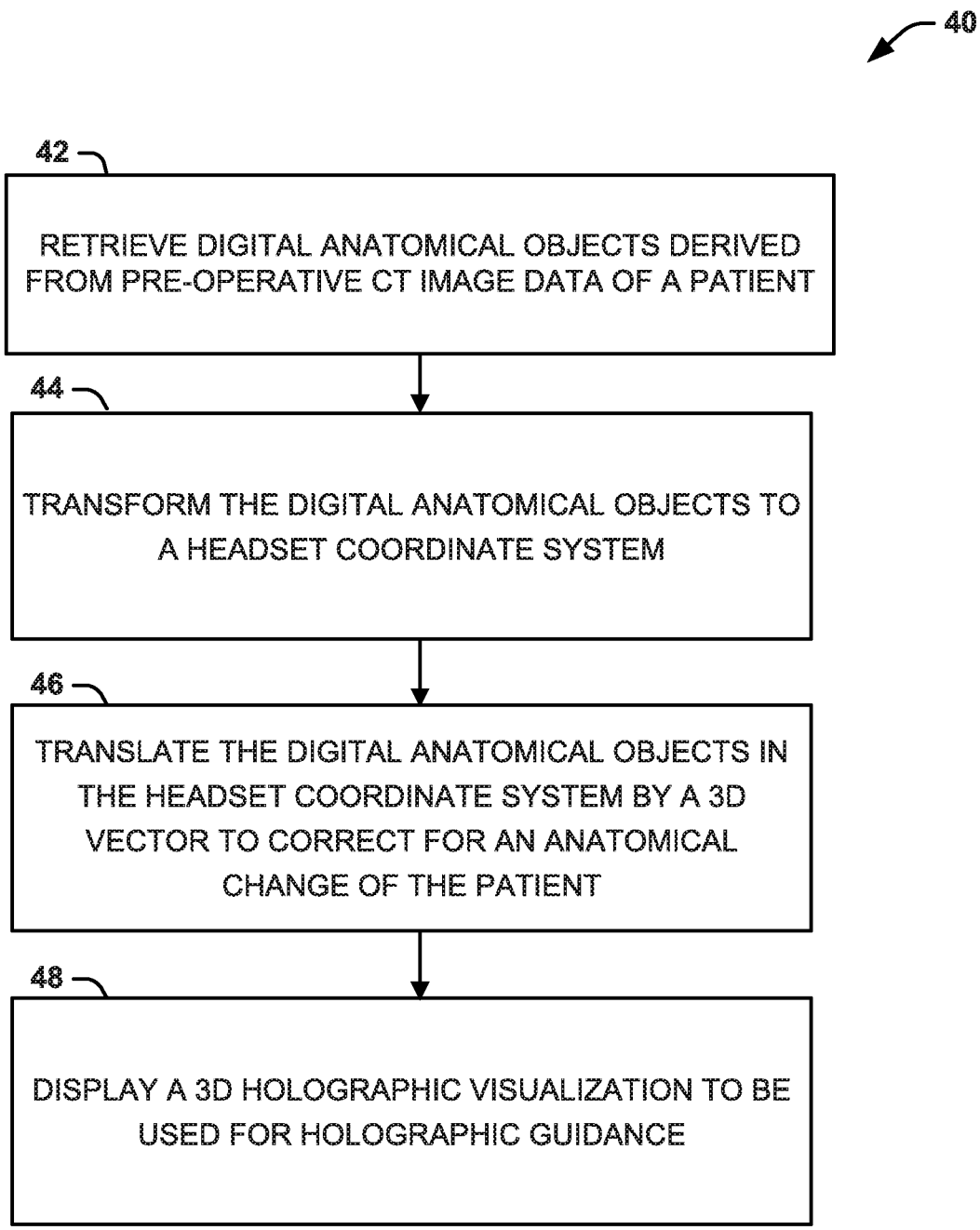

The method for providing live 3D holographic guidance and navigation for performing ultrasound-guided interventional procedures continues in the method 40 of FIG. 4. At step 42, digital anatomical objects (e.g., AO) derived from (e.g., by image segmentation) pre-operative computed tomography (e.g., PCT) image data of a patient can be received (by the head-mounted device 1). At step 44, the digital anatomical objects can be transformed (by the head-mounted device 1) to a headset coordinate system. At step 46, the digital anatomical objects in the headset coordinate system can be translated (by the head-mounted device 1) by a 3D vector to correct for an anatomical change in the patient. The 3D vector can be based on a 3D point selected by a user on the holographic ultrasound and correlated to the holographic anatomical objects. At step 48, a 3D holographic visualization can be displayed (by the head-mounted device 1) and used for holographic guidance. The 3D holographic visualization can include a 3D representation of the interventional device/instrument registered to a 3D holographic projection of a live ultrasound stream and a 3D holographic projection of the digital anatomical objects. The visualization can be stereoscopically projected onto the patient in congruence with the patient's physical anatomy as a visualization. The visualization can be scaled and/or moved according to an input from the head tracking mechanism 6 and/or an auditory input. The visualization can also include guidance control graphics and/or reference graphics to facilitate guiding the interventional device through the patient's anatomy.

V. Example Set-Up

Figure 5:
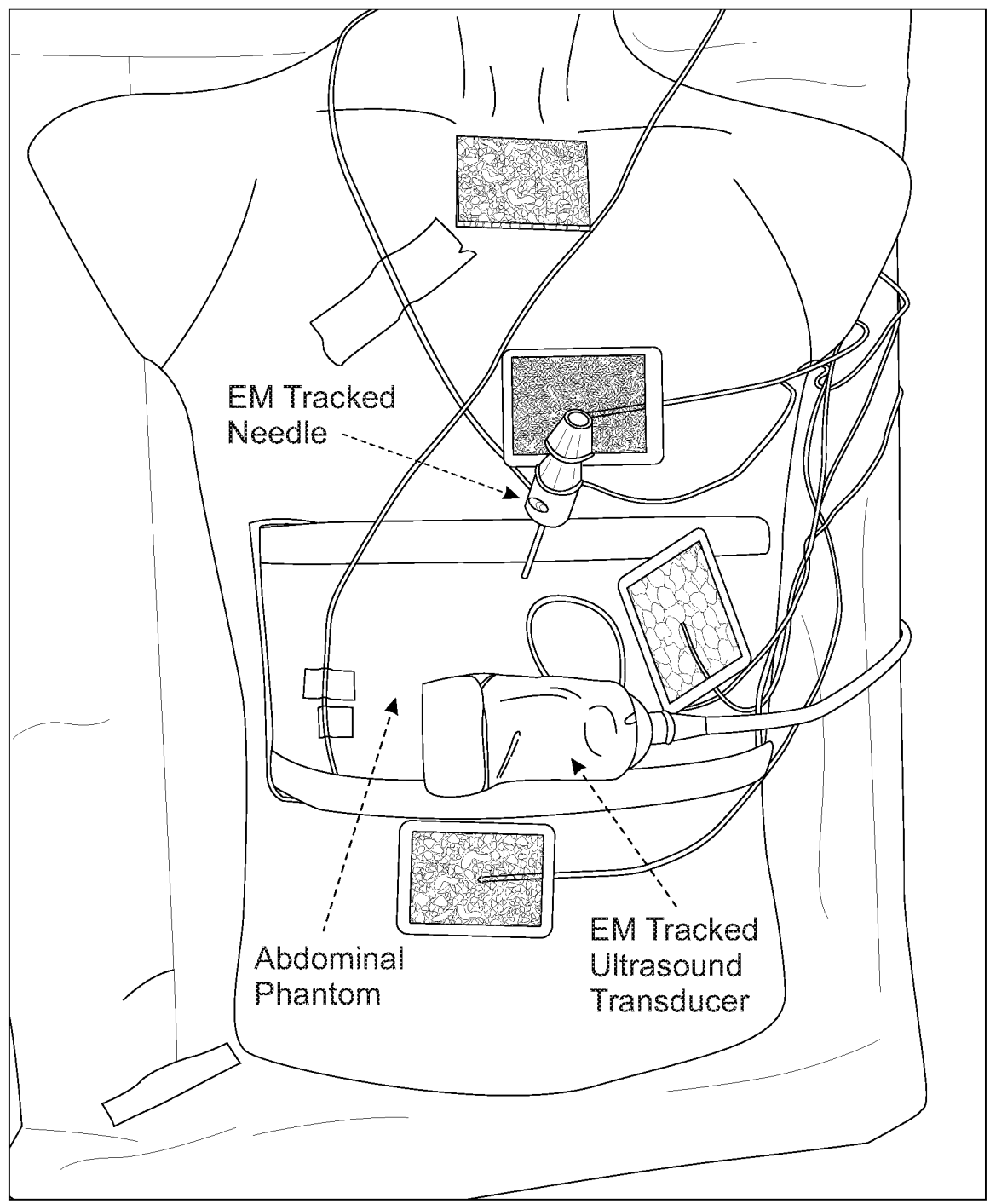
FIG. 5 is an image of components used for live 3D holographic guidance.
Figure 6:
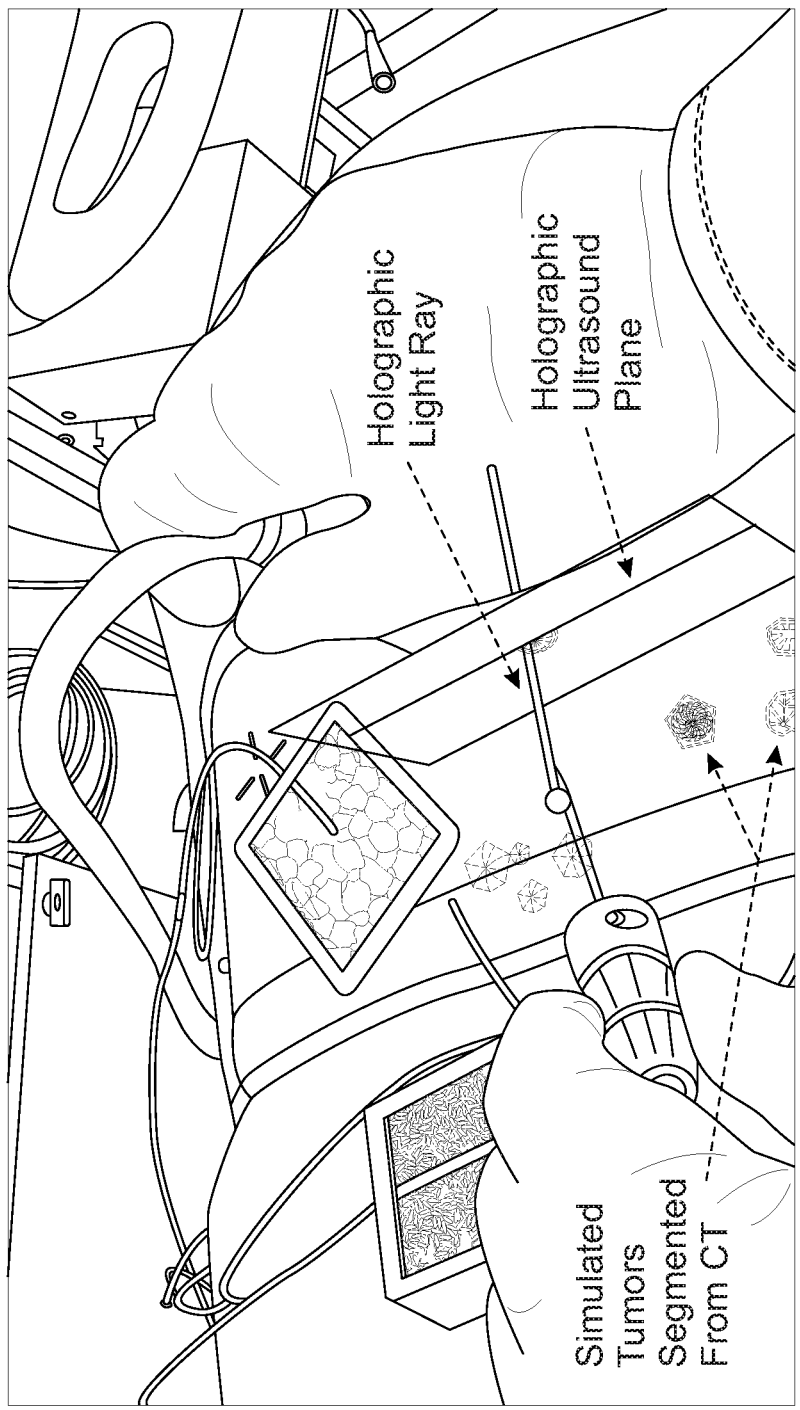
FIG. 6 is an image showing the example use of live 3D holographic guidance.
Figure 7:
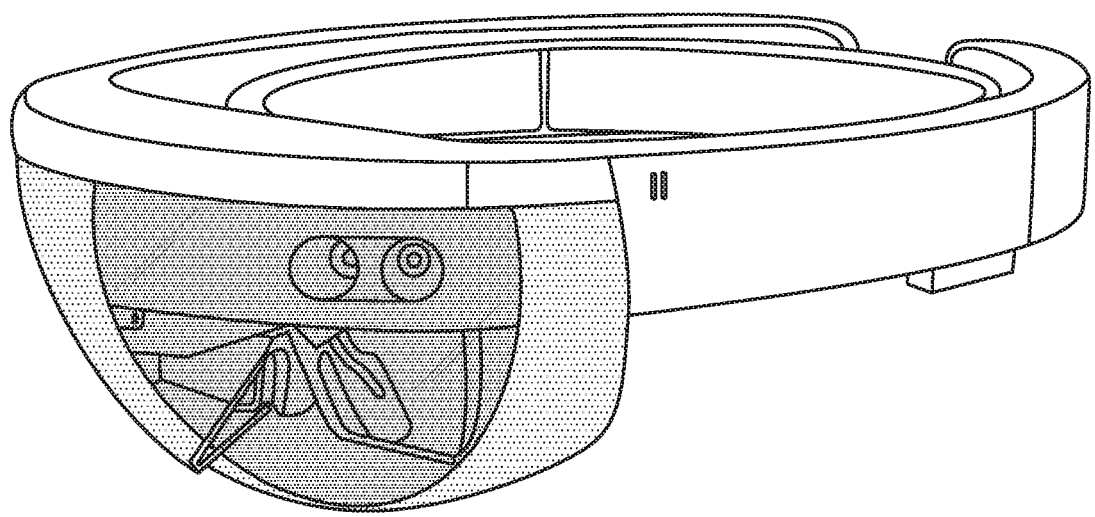
FIG. 7 is an image of an example head-mounted device.

FIGS. 5-7 show a bench experimental use of the system 10 described in FIG. 1. FIG. 5 shows a manikin body with an abdomen for a surgical procedure. Four location sensors (LS) are distributed at fiducial locations across the patient's body. An ultrasound probe and a surgical instrument are also provided, each with tracking sensors (T/PS and IDS). FIG. 6 shows use of the elements of FIG. 5 in connection with a holographic display. FIG. 7 shows the Microsoft HoloLens, which is used as the head-mounted device 1 to provide the holographic display of FIG. 6. Techniques that can be used in the Example are discussed below.

VI. Example Techniques

User Specified 3D Point Location on the Holographic Ultrasound Plane.

An operator can locate a point on a holographic ultrasound plane. A cursor location can be adjusted by "gazing" at the location on the plane. If the operator gazes at the same location for a period of time, a small sphere can be placed at that location. This location, for example, can be the center of a tumor as projected on the holographic ultrasound plane (HUP).

The point location on the HUP, $P_{hup}$, can be used for tissue targeting verification tests as follows. Suppose a 3D point is also located at the intersection of the interventional instruments HLR—a line segment extrapolated from the physical tip along the trajectory of said instrument—and the HUP, then the distance between these two points can be computed and reported in holographic text.

CT-Corrective Registration to Live Ultrasound at Homologous Point.

The point location, $P_{hup}$, can also be used to spatially register two hologram imaging types such as ultrasound (real-time planar) and CT (pre-procedure 3D volume). The center of a tumor, $P_{TCT}$, can be located in the pre-procedure processing stage. Since the CT and the HUP are both transformed to HoloLens (shown in FIG. 7) coordinates at the start of the procedure, the CT-derived hologram (which can contain not only the segmented tumor, but also organs and blood vessels) can be translated by a vector computed as $P_{TCT}-P_{hup}$. The distance of translation of the CT image can be recorded. If the CT data set has more than one tumor, each with an associated center point, then the correctional registration can be performed in a tumor-specific fashion. More generally, homologous points and features identified in the ultrasound and CT holograms can be used to improve the registration between the CT and the US image holograms, based on rigid affine transformations, and even elastic (non-rigid transformations) can be used.

Scale-Up of Fused (CT/US/HLR) Holographic Cartesian Volume.

With augmented and mixed reality (AR/MR), patient-specific holograms and device holograms are normally registered with each other (in holographic coordinates) and then stereoscopically projected onto (in registration with) the patient; whereas, conventional image guidance systems establish a correspondence between physical and displayed anatomical and device images, but display on a 2-D monitor and not the patient. For the holograms to be congruent with the physical space (patient coordinates), they must be at the unity (i.e., identity) scale. Projecting the device and anatomical (including the HUP) holograms to the patient provides the advantages of 1) optimal eye-hand coordination for navigating devices to targeting tissue, and 2) no needed to view the images on a separate 2D monitor, and 3) congruence of the augmented and physical reality. For some applications, this can provide improved 3D visualization of the holographic content, particularly for optical see through devices (OSD). For OSD, the quality for visualizing the holograms is dependent on its background, and projecting on to the patient may not be the optimal, in some cases.

Holograms that are projected onto the patient can also be translated (e.g., to a space that is anterior/above to the patient) and scaled (by a factor of 2) to a location that has an improved background or that is more comfortable while maintaining 1) registration between device and multi-modality holograms, 2) eye-hand coordination for device navigation to the target. When the holograms are scaled and translated, the eye-hand coordination is maintained, but not as correlated as when the holograms are projected to the patient. The holograms could also be rotated relative the physical anatomy, but this would further de-correlate the eye-hand coordination. For example, the holographic ultrasound plane can be rotated to follow the operator's viewing direction, i.e., always facing the operator. This would de-couple eye-hand coordination but precludes the operator from looking back-and-forth to a 2-D display where the said display is in a fixed location.

The operator can optionally switch back- and forth between the scale-up/translated/rotated views and the projection to the patient. This can be implemented with a voice command or other input on the head-mounted display, such as a holographic dashboard.

Depth Adjustment to Un-Scale Holographic Ultrasound Plane.

The depth adjustment knob on ultrasound equipment controls changes the scale of the image. An increase depth (e.g., to 8 cm) will scale and display the ultrasound image on the 2D monitor such that vertical length of the image (e.g. 1024 pixels) will correspond to 8 cm. Therefore, the frame grabbed used herein image will also correspond to 8 cm of depth. In this instance HUP must also be scaled according to the adjustments of the depth.

This can be done according to with voice commands on the head-mounted display. The operator can specify the depths in other words (e.g., "eight" or "ten") to specify the depth setting. This will maintain the scale of the HUP and physical field (assuming an identity scale factor) when holographically projecting on to the patient.

Calibration of Holographic Image Plane to Physical Transducer.

For locating the holographic ultrasound plane, HUP, in relation to the ultrasound transducer, an adjustable 6 degree of freedom transformation can be provided in the manufacturing so that the HUP accurately extends from the physical transducer. Six slider bar inputs can be used to interactively determine the transformation. The transformation from the sliders is used to locate the center tip of the ultrasound array. The HUP is delineated with holographic lines to facilitate the adjustment of the 3 axis rotation and 3 axis translation. The 6 degree of freedom transformation for a tracked transducer can be stored for individual transducer types and manufacturers. The ultrasound image is transformed to correspond to the ultrasound probe.

Methods for Visualization of Holographic CT and Ultrasound.

When combining the HUP and 3D CT, the CT holograms (based on segmentation) results can potentially obscure the echogenic lesions on the HUP (VIDEO: SCALE UP ADJ CT). This can be prevented by using transparent materials for the CT-based holograms (e.g., tumors, organs, and blood vessels). Another approach is to project the surfaces as a wire frame shader so that the echogenic lesion can be viewed in congruence with the CT hologram. Yet another approach is to toggle on and off the CT based holograms to view echogenic features on the HUP.

From the above description, those skilled in the art will perceive improvements, changes and modifications. Such The following is claimed:

1. A method comprising:
   receiving, by a physical head-mounted device comprising a processor and a head-tracking mechanism, live tracking data from a procedure in 3D Cartesian coordinates of a navigation system,
   wherein the live tracking data comprises a position and orientation of:
      a tracked physical ultrasound transducer/probe connected to an ultrasound system,
      a tracked physical interventional device/instrument, and
      physical fiducial location sensors at specific anatomical locations on a physical patient;
   receiving, by the physical head-mounted device, a live ultrasound image stream acquired by the physical ultrasound transducer/probe connected to the ultrasound system;
   transforming, by the head-mounted device, the live ultrasound image stream to a headset coordinate system;
   transforming, by the head-mounted device, the live tracking data to the headset coordinate system;
   displaying, in a head-mounted display of the head mounted device, a live holographic projection of the live ultrasound image stream in the headset coordinate system, wherein the live holographic projection of the ultrasound image stream is based on the tracked position and tracked orientation of the transducer/probe, wherein the live holographic projection is scaled to the physical anatomy consistent with an operator's view assessed with the head-tracking mechanism;
   retrieving, by the head mounted device, digital anatomical objects derived from pre-operative 3D computed tomography (CT) image data of the physical patient, wherein the CT image data is in 3D coordinates of a CT coordinate system;
   transforming, by the head-mounted device, the digital anatomical objects from the 3D CT coordinate system to the headset coordinate system;
   translating, by the head mounted device, the anatomical objects in the headset coordinate system by a 3D vector computed based on a 3D point location on the live holographic projection of the live image stream and a corresponding point within the stored pre-operative CT image data in the headset coordinate system to correct for a live anatomical motion of the physical patient during the procedure; and
   displaying, in the head mounted display of the head mounted device, a holographic visualization comprising a holographic representation of the tracked physical interventional device/instrument congruent with the registered holographic projection of the live ultrasound image stream and the holographic anatomical objects derived from CT, wherein the holographic visualization is used to navigate the tracked physical ultrasound transducer/probe and guide the physical interventional device/instrument to a therapeutic target during the procedure.

2. The method of claim 1, wherein the live anatomical motion comprises respiratory motion or gross patient motion.

3. The method of claim 1, wherein the displaying further comprises displaying a holographic representation of the interventional device/instrument with guidance control graphics within the 3D anatomical holographic projections comprising reference graphics related to an operative site comprising at least a portion of the portion of the patient's physical anatomy, wherein the guidance control graphics and the reference graphics are configured to aid in navigating the interventional device/instrument through the portion of the patient's physical anatomy to the therapeutic point.

4. The method of claim 1, wherein the physical interventional device/instrument is utilized in a percutaneous non-vascular medical procedure, an endovascular percutaneous medical procedure, or an open surgical procedure.

5. The method of claim 1, wherein the holographic anatomical objects derived from CT are projected to enable visualization without occlusion of the live holographic projection of the live ultrasound image stream.

6. The method of claim 1, wherein a 3D point is identified and located on the registered holographic projection of the live ultrasound image stream based on an operator input, wherein the 3D point is a center of an imaged tumor or blood vessel cross section.

7. The method of claim 1, wherein the live tracking data is based on electromagnetic tracking of electromagnetic sensor coils or optical tracking of reflective markers.

8. The method of claim 7, wherein the electromagnetic sensor coils and/or the reflective markers are located within and/or on the tracked physical ultrasound transducer/probe, the tracked physical interventional device/instrument, and the physical fiducial location sensors.

9. The method of claim 1, wherein the holographic visualization is stereoscopically projected onto the patient in congruence with the patient's physical anatomy, the ultrasound transducer/probe, and the physical interventional device/instrument.

10. The method of claim 9, further comprising, upon receiving an operator input, projecting, by the head mounted device, the visualization not congruent with the patient's physical anatomy and/or the physical ultrasound transducer/probe and/or the physical interventional device/instrument while maintaining co-registration of the holographic projections.

11. The method of claim 9, further comprising, upon receiving an operator input, continuously realigning, by the head mounted device, the visualization to re-orient the virtual display so that it always faces the operator based on tracking data from the head mounted device.

12. The method of claim 9, further comprising maintaining a co-registration of a holographic light ray, the registered holographic projection of the live ultrasound image stream, and the holographic anatomical objects derived from CT when the visualization is translated, rotated, and/or scaled relative to the physical anatomy.

13. The method of claim 12 wherein, the intersection of the holographic light ray and the registered holographic projection of the live ultrasound image stream is displayed as a spherical point of intersection.

14. The method of claim 9, further comprising, by limiting or preventing the rotation of the holographic scene to maintain hand-eye coordination of the operator when navigating the ultrasound transducer/probe and the interventional device/instrument.

15. The method of claim 1, wherein the registered holographic projection of the live ultrasound image stream is pre-calibrated with local rotation, translation, and scaling to extend from the tracked physical interventional device/instrument in congruence with the patient's physical anatomy.

16. The method of claim 15, wherein the registered holographic projection of the live ultrasound image stream is automatically re-calibrated with the local rotation, translation, and scaling so that it maintains congruence with the patient's physical anatomy when the operator adjusts a scale/depth setting on the physical ultrasound system.

17. A system comprising:
a computing device comprising a memory to store digital anatomical objects derived from pre-operative 3D computed tomography (CT) image data of a physical patient, wherein the CT image data is in 3D coordinates of a CT coordinate system;
a head-mounted device, comprising a processor, a head mounted display, and a head-tracking mechanism, to:
  receive live tracking data from a procedure in 3D Cartesian coordinates of a navigation system,
  wherein the live tracking data comprises a position and orientation of:
    a tracked physical ultrasound transducer/probe connected to an ultrasound system,
    a tracked physical interventional device/instrument, and
    physical fiducial location sensors at specific anatomical locations on a physical patient;
  receive a live ultrasound image stream acquired by the physical ultrasound transducer/probe connected to the ultrasound system;
  transform the live ultrasound image stream to a headset coordinate system;
  transform the live tracking data to the headset coordinate system;
  display, in the head-mounted display, a live holographic projection of the live ultrasound image stream in the headset coordinate system, wherein the live holographic projection of the ultrasound image stream is based on the tracked position and tracked orientation of the transducer/probe, wherein the live holographic projection is scaled consistent with an operator's view assessed with the head-tracking mechanism;
  retrieve the digital anatomical objects;
  transform the digital anatomical objects from the 3D coordinates of the CT coordinate system to the headset coordinate system;
  translate the anatomical objects in the headset coordinate system by a 3D vector computed based on a 3D point location on the live holographic projection of the live image stream and a corresponding point within the stored pre-operative CT image data in the headset coordinate system to correct for a live anatomical motion of the physical patient during the procedure; and
  display, in the head mounted display, a holographic visualization comprising a holographic representation of the tracked physical interventional device/instrument congruent with the registered holographic projection of the live ultrasound image stream and the holographic anatomical objects derived from CT, wherein the holographic visualization is used to position the tracked physical ultrasound transducer/probe and guide the physical interventional device/instrument to a therapeutic target.

18. The system of claim 17, wherein the live tracking data is based on electromagnetic tracking of electromagnetic sensor coils and/or optical tracking of reflective markers, and
wherein the electromagnetic sensor coils and/or the reflective markers are located within and/or on the tracked physical ultrasound transducer/probe, the tracked physical interventional device/instrument, and the physical fiducial location sensors.

19. The system of claim 17, wherein the holographic visualization is stereoscopically projected onto the patient in congruence with the patient's physical anatomy, the ultrasound transducer/probe, and the physical interventional device/instrument.

20. The system of claim 19, further comprising, upon receiving an operator input, projecting, by the head mounted device, the visualization not congruent with the patient's physical anatomy and/or the physical ultrasound transducer/probe and/or the physical interventional device/instrument while maintaining co-registration of the holographic projections.

21. The system of claim 19, further comprising, upon receiving an operator input, continuously realigning, by the head mounted device, the visualization to always face the operator based on tracking data from the head mounted device.

22. The system of claim 19, further comprising maintaining a co-registration of a holographic light ray, the registered holographic projection of the live ultrasound image stream, and the holographic anatomical objects derived from CT when the visualization is translated, rotated, and/or scaled relative to the physical anatomy.

23. The system of claim 22 wherein, the intersection of the holographic light ray and the registered holographic projection of the live ultrasound image stream is displayed as a spherical point of intersection.

* * * * *